(12) United States Patent
Hilmer et al.

(10) Patent No.: US 11,291,234 B2
(45) Date of Patent: Apr. 5, 2022

(54) FOOD COMPOSITION

(71) Applicant: SYMRISE AG, Holzminden (DE)

(72) Inventors: Jens-Michael Hilmer, Holzminden (DE); Eric Gruber, Holzminden (DE); Natalia Konya, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/956,205

(22) PCT Filed: Dec. 22, 2017

(86) PCT No.: PCT/EP2017/084568
§ 371 (c)(1),
(2) Date: Jun. 19, 2020

(87) PCT Pub. No.: WO2019/120593
PCT Pub. Date: Jun. 27, 2019

(65) Prior Publication Data
US 2020/0329750 A1    Oct. 22, 2020

(51) Int. Cl.
| | |
|---|---|
| A23L 27/00 | (2016.01) |
| A23L 29/30 | (2016.01) |
| A23P 10/30 | (2016.01) |
| A23L 29/25 | (2016.01) |
| A23P 20/18 | (2016.01) |
| A23D 7/005 | (2006.01) |

(Continued)

(52) U.S. Cl.
CPC ............ *A23L 27/72* (2016.08); *A23D 7/0053* (2013.01); *A23D 7/02* (2013.01); *A23G 4/068* (2013.01); *A23G 4/10* (2013.01); *A23G 4/20* (2013.01); *A23L 2/56* (2013.01); *A23L 2/60* (2013.01); *A23L 29/25* (2016.08); *A23L 29/35* (2016.08); *A23L 29/37* (2016.08); *A23P 10/30* (2016.08); *A23P 20/18* (2016.08); *A61K 9/0056* (2013.01); *A61K 47/26* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,956,926 A | 10/1960 | Grief | |
| 4,515,769 A * | 5/1985 | Merritt | A23G 4/043 |
| | | | 131/274 |

(Continued)

FOREIGN PATENT DOCUMENTS

| | | |
|---|---|---|
| EP | 0 859 554 A1 | 8/1998 |
| EP | 1 214 892 A1 | 6/2002 |

(Continued)

OTHER PUBLICATIONS

Chaven et al. Maltodextrin, Fat Replacer, Encyclopedia of Food and Health, 2016). (Year: 2016).*

(Continued)

*Primary Examiner* — Melissa S Mercier
(74) *Attorney, Agent, or Firm* — Marshall, Gerstein & Borun LLP (57) ABSTRACT

The present invention relates to a food composition, a process for the production of the food composition, a food composition producible by the method according to the invention, the use of the food composition and products comprising the food composition according to the invention.

22 Claims, 3 Drawing Sheets

Schematic representation of the food composition according to the invention (51) Int. Cl.
*A23D 7/02* (2006.01)
*A23G 4/06* (2006.01)
*A23G 4/10* (2006.01)
*A23G 4/20* (2006.01)
*A23L 2/56* (2006.01)
*A23L 2/60* (2006.01)
*A61K 9/00* (2006.01)
*A61K 47/26* (2006.01)

(56) References Cited

U.S. PATENT DOCUMENTS

| | | | |
|---|---|---|---|
| 5,965,181 A | 10/1999 | Barkalow et al. | |
| 6,190,705 B1 | 2/2001 | Richey | |
| 8,367,111 B2 * | 2/2013 | Venkatesh | A61K 9/5084 424/489 |
| 2008/0299249 A1 * | 12/2008 | Hirt | A23G 4/20 426/5 |
| 2009/0150231 A1 | 6/2009 | Jani et al. | |
| 2010/0266685 A1 * | 10/2010 | Machinek | A23L 27/72 424/463 |
| 2016/0029659 A1 * | 2/2016 | Colle | A23G 4/20 426/5 |
| 2018/0070614 A1 * | 3/2018 | Marshall-Hill | A23L 2/54 |

FOREIGN PATENT DOCUMENTS

| | | |
|---|---|---|
| EP | 1 537 791 A1 | 6/2005 |
| WO | WO-97/16078 A1 | 5/1997 |
| WO | WO-98/23165 A1 | 6/1998 |
| WO | WO-2006/127494 A2 | 11/2006 |

OTHER PUBLICATIONS

Arctander, "Perfume and Flavor Chemicals," self-publication (1969).
Internatioanl Search Report and Written Opinion for Application No. PCT/EP2017/084568, dated Mar. 27, 2018.
Surburg et al., "Common Fragrance and Flavor Materials," 6th Edition, Wiley-VCH, Weinheim (2016).

* cited by examiner

Figure 1: Schematic representation of the food composition according to the invention Figure 2: Schematic diagram of an alternative design of the food composition

Figure 3: Sample 1

Figure 4: Sample 2

Figure 5: Sample 3

FOOD COMPOSITION

CROSS-REFERENCE TO RELATED APPLICATIONS

This is a U.S. National Phase of International Application No. PCT/EP2017/084568, filed Dec. 22, 2017.

FIELD OF THE INVENTION

The present invention is in the field of food flavouring and relates to a food composition, a process for producing the food composition according to the invention, a food composition obtainable by the process according to the invention, the use of the food composition and products comprising the food composition according to the invention. The focus of the present invention is in particular to obtain a food composition with a high flavour and aroma charge and a coincident and congruent release of flavour and aroma substances.

STATE OF THE ART

Flavours are often added to foods and foodstuffs to round off the flavour profile. On the one hand, they ensure a consistent taste, and on the other hand, aromas can improve, strengthen, round off the taste or make it unique and unmistakable. The aroma originating from a specific source, e.g. a fruit, is not a chemically uniform substance, but is composed of a large number of different chemical components, which only in their entirety produce the sensory result of the natural aroma of a foodstuff. The overall sensory impression of a foodstuff, in turn, is determined by odour or aroma substances on the one hand and flavourings on the other. The taste impressions perceived by the tongue include sweet, sour, salty, bitter and umami. Aromatic substances, on the other hand, are perceived by the senses of smell in the mouth-throat area, not by the tongue. When chewing, flavours and aromas are perceived simultaneously and reinforce each other. Aromatic and taste substances are perceived together and are evaluated in the brain. For example, there is no strawberry taste; we perceive a mixture of flavours that remind us of strawberries together with a mixture of sweet and roughly sour taste. Ultimately, it is the simultaneous interaction of aroma and taste substances that determines whether a food product tastes good or not.

The coating of citric acid with fat has been known since the 1960s, such a coating is described for example in U.S. Pat. No. 2,956,926.

EP 1 214 892 A1 reveals a moisture and oxygen stable composition comprising inert core particles partially or fully coated with at least one active compound encapsulated in a carbohydrate matrix. The carbohydrate matrix comprises 5 to 70% by weight of high molecular weight film forming carbohydrate, 5 to 30% by weight of mono-, di- and trisaccharides, and 10 to 30% by weight of maltodextrin, based on the total weight of the carbohydrate matrix. The inert core particles can be selected from edible materials, for example plant particles, crystal products such as sugar crystals and salt crystals, fibres such as organic and artificial fibres, plant seeds, etc. However, there is no doctrine of coincident and congruent release of aroma and flavourings in the composition.

EP 1 537 791 A1 describes composite particles which have been coated with two different components in succession, which when dissolved in water cause two different successive changes in food. The composite particles comprise a core and a shell, each of which contains an optically and/or organoleptically modifying component. The organoleptically modifying components are flavouring agents, flavour enhancers, flavour precursors or the like. Exemplary described are composite particles comprising citric acid particles as the core which are coated with an aqueous solution containing 40% maltodextrin, 2% strawberry flavour and 0.2% dye by spraying. A second layer of gum arabic is then applied for inertization.

EP 0 859 554 A1 reveals a process for the production of granules in which a flavour or fragrance emulsion is sprayed in a submersed way in a fluidised bed of fluidised core material. The core material is a carbohydrate, e.g. a sugar such as glucose, lactose, sucrose, starch or degraded starch, or a sugar alcohol such as isomalt, or pectin, hydrolysed vegetable protein etc. The carrier material for the spray emulsion is chemically modified starch, degraded starch such as maltodextrins, natural resins, exudates such as gum arabic, gelatine or plant extracts such as carrageenan or alginates in water or water/alcohol mixtures.

However, none of the above-mentioned state of the art publications contains a teaching on a composition in which a coincident and congruent sensory profile of flavouring and aromatic substances is realized.

The aim of the present invention was to provide a food composition which, on the one hand, has a high loading of flavouring and aromatic substances and, on the other hand, with which a coincident and congruent sensory profile of flavouring and aromatic substances can be realised so that the food and foodstuff to be flavoured has an authentic and rounded taste, for example a fruit flavour.

DESCRIPTION OF THE INVENTION

The present problem is solved by the subject-matter of the independent patent claims. Preferred formulations result from the wording of the dependent patent claims and the following description.

A first subject matter of the present invention concerns a food composition comprising
  a core component, and
  a coating,
wherein the coating comprises a carbohydrate matrix in which at least one flavouring agent is enclosed, and the carbohydrate matrix comprises at least one sugar alcohol, which is present in an amount of 0.1 to 30% by weight, preferably 0.1 to 20% by weight, based on the total weight of the carbohydrate matrix.

Another subject of the present invention concerns a process for the production of the food composition, comprising the steps:
(i) Providing an emulsion comprising a carbohydrate matrix in which at least one flavouring agent and/or flavour is included, and the carbohydrate matrix comprises at least one sugar alcohol present in an amount of 0.1 to 20% by weight based on the total weight of the carbohydrate matrix;
(ii) Application of the emulsion provided in step (i) to the core component by spray coating;
(iii) Drying of the food composition obtained in step (ii)
(iv) If necessary, repeat steps (ii) and (iii) continuously.

Furthermore, a subject matter of the present invention relates to a food composition, producible or prepared according to the manufacturing process according to the above-mentioned invention.

Another aspect of the present invention relates to the use of the food composition according to the invention for flavouring or reconstituting the flavour of foodstuffs, food supplements, beverage products, semi-finished products, oral hygiene products, cosmetic or pharmaceutical products or products for animal nutrition.

Ultimately, the present invention relates to food, food supplements, beverage products, semi-finished products, oral hygiene products, cosmetic or pharmaceutical products or products for animal nutrition which comprise the food composition according to the invention.

DETAILED DESCRIPTION OF THE INVENTION

Figure 1:
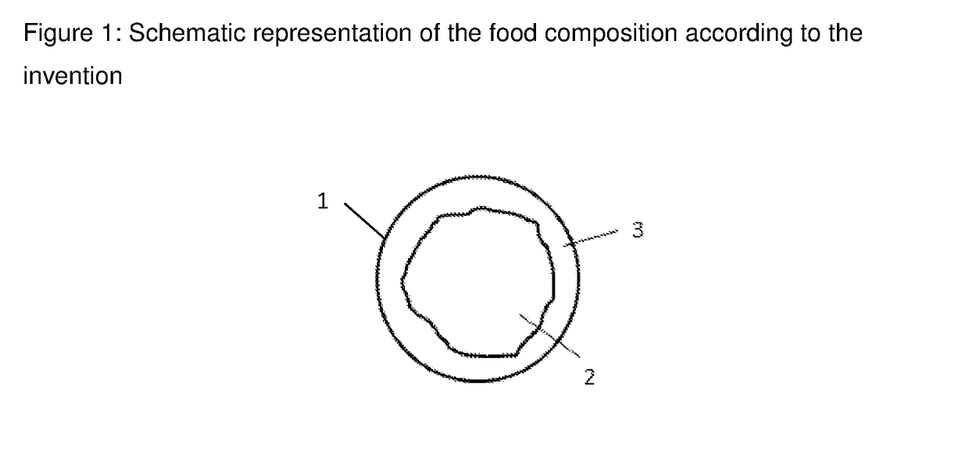
FIG. 1 is a schematic representation of the structure of the food composition according to the invention.
Figure 2:
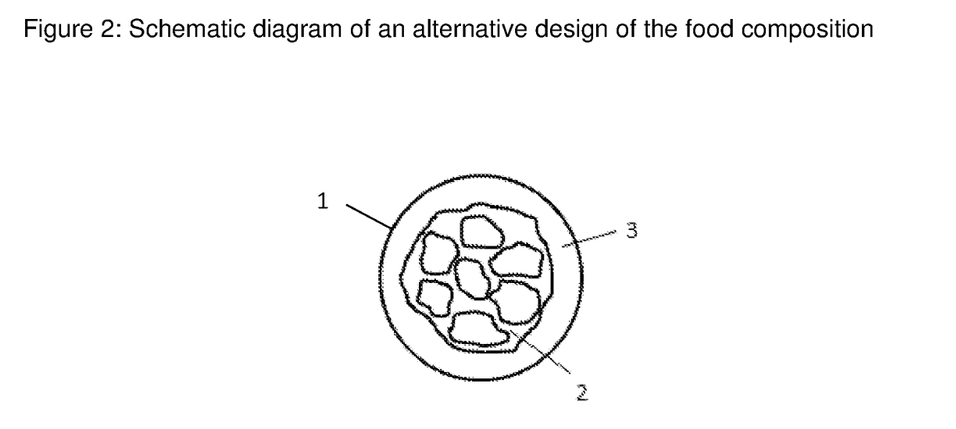
FIG. 2 is a schematic representation of the structure of an alternative embodiment of the food composition claimed in the invention.

The present invention relates to a food composition 1, comprising
a core component 2, and
a coating 3,
wherein the coating comprises a carbohydrate matrix in which at least one flavouring agent is enclosed, and the carbohydrate matrix comprises at least one sugar alcohol present in an amount of 0.1 to 20% by weight based on the total weight of the carbohydrate matrix.

The core component 2 of the food composition according to the invention comprises at least one flavouring component selected from the group consisting of fruit acids, ascorbic acid, menthol and NaCl or KCl.

The term fruit acids is a collective term for the organic hydroxycarboxylic acids and dicarboxylic acids found in fruit. Fruit acids and their salts are used in large quantities as acidifying agents in foodstuffs. Preferably the fruit acids are selected from the group consisting of: malic acid, citric acid, fumaric acid, gluconic acid, glycolic acid, α-hydroxycaprylic acid, mandelic acid, tartaric acid, oxalic acid and salicylic acid, as well as the enantiomers (D- and L-form) and the salts of the above mentioned fruit acids, as well as lactate. Citric acid is preferably used as the core component.

The fruit acids or their salts are used either pure or in combination with each other or in combination with other components to form the core component. According to the present invention, fruit acids are preferably used. Other raw materials suitable for forming the core component include menthol and menthol derivatives as well as the salts NaCl and KCl used for a salty taste.

A pre-treatment of the fruit acids to produce the core component is not necessary. The fruit acids or their salts are used in solid, crystalline form.

The aforementioned crystals that form the core component are individually coated with the coating, so that the core consists of a single crystal surrounded by the coating (see FIG. 1). In an alternative design, the crystals are made into an agglomerate, i.e. an accumulation of crystals, which forms the core and which is then coated with the coating (see FIG. 2).

The fruit acids or their salts described above are used to achieve an acidic and thus refreshing taste and to round off the aroma, because it is the acids that allow the aroma substances to develop their flavour.

With the food composition according to the invention, a high fruit acid concentration in the core is advantageously realizable. With the state of the art particles, a loading of a maximum of 5 to 7 weight percent fruit acid is possible. At a higher fruit acid content, spray drying is no longer possible due to sticking. In contrast, in the present invention, the fruit acid content in the core is up to 99% by weight, preferably 40 to 60% by weight and most preferably at least 50% by weight, based on the total weight of the food composition.

The core component usually has an average particle size of 0.1 to 10 mm, preferably an average particle size of 0.4 to 1.2 mm and most preferably an average particle size of 0.5 to 1.0 mm, especially 0.6 mm.

In a preferred design, the core component consists of a citric acid crystal with an average particle size of 0.1 mm to 10 mm, preferably with an average particle size of 0.4 to 1.2 mm and most preferably with an average particle size of 0.6 mm.

The coating 3 of the food composition according to the invention, which surrounds the core 2, comprises a carbohydrate matrix.

The carbohydrate matrix of the coating of the food composition according to the invention comprises at least one flavouring and/or at least one aroma.

Flavouring substances are chemically defined substances with flavouring properties. In general, flavouring substances can be divided into two sub-categories:

Synthetic flavourings are produced by means of synthetic processes. They are either nature-identical flavouring substances or artificial flavouring substances.

The nature-identical flavourings follow a model found in nature and their molecular structure corresponds to this model, e.g. synthetically produced vanillin. Artificial flavourings, on the other hand, have no model in nature.

Natural flavouring substances are flavouring substances obtained by legally prescribed physical (e.g. distillation and extraction), enzymatic or microbiological processes. Starting materials for production may be of vegetable, animal or microbiological (e.g. yeasts) origin; both the starting materials and the production processes are natural.

Flavours in turn usually consist of several ingredients. These are flavouring components (flavouring substances, flavouring extracts, thermally produced reaction flavourings, smoke flavourings, flavour precursors, other flavourings or mixtures thereof).

The at least one flavouring or aromatic substance or flavour according to the invention may also be a mixture of at least two flavouring and/or aromatic substances. Preferably it is a mixture of at least three, four or more than five flavouring substances and/or aromas. In most cases, aroma mixtures are a mixture of many aroma substances and/or aromas. This has the advantage that the taste profile of the food composition according to the invention can be influenced. An aroma usually contains solvents or carriers in addition to the actual flavouring substances contained in it, so as to achieve a dosing capability and dosability.

Suitable flavouring substances for the production of the food composition according to the present invention can be found, for example, in Steffen Arctander, "Riechstoffe" in "Perfume and Flavor Chemicals", self-publication, Montclair, N. J. 1969; H. Surburg, J. Panten, in "Common Fragrance and Flavor Materials", 6th Edition, Wiley-VCH, Weinheim 2016, for example: esters (saturated or unsaturated) such as ethyl butyrate, allyl capronate, benzyl acetate, methyl salicylate; organic acids (saturated and unsaturated) such as butyric acid, acetic acid, methyl butyric acid, caproic acid; alcohols (saturated and unsaturated) such as e.g. ethanol, propylene glycol, octenol, cis-3-hexanol, benzyl alcohol, phenylethyl alcohol; aldehydes (saturated and unsaturated) such as acetaldehyde, isobutyraldehyde, nonadienal, benzaldehyde, 3-phenylacetaldehyde; ketones such as menthone; ethers such as 4-hydroxy-5-methylfuranone, 3-hydroxy-4,5-dimethyl-2-(5H)-furanone, 2,5-dimethyl-3-hydroxy-2(3H)-furanone, 2(5)-ethyl-4-hydroxy-5(2)-methyl-3 (2H)-furanone, p-methoxybenzaldehyde, guaiacol, methoxyvinylphenol; acetals such as Acetaldehyde diethyl acetal; lactones such as gamma-decalactone; terpenes such as limonene, linalool, terpinene, terpineol, citral (geranial and neral), menthol; sulfides and disulfides such as dimethyl sulfide, difurfuryl disulfide, methylthiopropanal; thiols such as e.g. methylfuranthiol; pyrazines and pyrrolines such as methylpyrazine, acetylpyrazine, 2-propionylpyrroline, 2-acetylpyrroline, acetophenone, allyl capronate, alpha-ionone, beta-ionone, anisaldehyde, anisyl acetate, anisyl formate, benzaldehyde, benzothiazole, benzyl acetate, benzyl alcohol, Benzyl benzoate, beta-ionone, butyl butyrate, butyl capronate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethylanthranilate, dimethylanthranilate, dodecalactone, ethoxyethyl acetate, ethyl butyric acid, ethyl butyrate, ethyl caprinate, ethyl capronate, ethyl crotonate, ethyl furaneol, ethyl guaiacol, ethyl isobutyrate, ethyl isovalerianate, Ethyl lactate, ethyl methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruitaldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl capronate, trans-2-hexenyl capronate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerianate, isobutyl butyrate, isobutyraldehyde, isoeugenol methyl ether, isopropylmethylthiazole, lauric acid, leavulinic acid, linalool, linalool oxide, linalyl acetate, menthol, menthofuran, methyl anthranilate, methyl butanol, methyl butyric acid, 2-methyl butyl acetate, methyl capronate, methyl cinnamate, 5-methylfurfural, 3,2,2-methylcyclopentenolone, 6,5,2-methylheptenone, methyl dihydrojasmonate, methyl jasmonate, 2-methylmethylbutyrate, 2-methyl-2-pentenolic acid, methylthiobutyrate, 3,1-methylthiohexanol, 3-methylthiohexyl acetate, nerol, nerylacetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentandione, phenylethyl acetate, phenylethyl alcohol, phenylethyl alcohol, phenylethyl isovalerianate, piperonal, propionaldehyde, propyl butyrate, pulegone, pulegol, sinensal, sulfurol, terpinols, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-Dimethyl-4-hydroxy-3(2H)-furanone and its derivatives (preferably homofuraneol (=2-ethyl-4-hydroxy-5-methyl-3 (2H)-furanone), homofuronol (=2-ethyl-5-methyl-4-hydroxy-3(2H)-furanone and 5-ethyl-2-methyl-4-hydroxy-3 (2H)-furanone), maltol and maltol derivatives (preferably ethylmaltol), coumarin and coumarin derivatives, gamma-lactones (preferably gamma-undecalactone, gamma-nonalactone, gamma-decalactone), delta-lactones (preferably 4-methyl-deltadecalactone), massoilactone, delta-decalactone, tuberolactone), methylsorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, isoamyl acetate, ethyl butyrate, n-butyl butyrate, isoamyl butyrate, ethyl 3-methyl butyrate, ethyl n-hexanoate, allyl n-hexanoate, n-butyl n-hexanoate, ethyl n-octanoate, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan 2-methyl-3-furanthiol, bis(2-methyl-3-furyl)disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-Hydroxy-4-methyl-5-ethyl-2 (5H)-furanone, cinnamic aldehyde, cinnamic alcohol, methyl salicylate, isopulegol and (here not explicitly mentioned) stereoisomers, enantiomers, position isomers, diastereomers, cis/trans isomers or epimers of these substances.

The flavours used according to the invention are selected from the group consisting of pineapple flavour, apple flavour, aronia flavour, citrus flavour, strawberry flavour, cherry flavour, vanilla flavour, passion fruit flavour, pear flavour, mango flavour, kiwi flavour, hibiscus flavour, Elderberry flavour, flavours from vegetables such as cucumber, carrot, asparagus, tomato, onion, celery, spinach, flavours from herbs such as dill, parsley, basil, mint, flavours from spices such as ginger, coffee and tea.

The flavouring and/or aromatic substance(s) is/are usually added (including solvents or carriers, if necessary) in an amount of 0,01 to 30% based on the total weight of the carbohydrate matrix, preferably in an amount of 10 to 20% based on the total weight of the carbohydrate matrix.

The content of flavouring and/or aromatic substances in the carbohydrate matrix can be increased by reducing the content of filler, for example maltodextrin.

Furthermore, the carbohydrate matrix includes a sugar alcohol. Sugar alcohols are used in the food industry as sugar substitutes as sweeteners; they taste sweet but are not cariogenic. The use of sugar in the carbohydrate matrix is known from the state of the art: Sugar increases the shelf life of the product by a high oxygen barrier, on the one hand by protecting the volatile flavourings from escaping and on the other hand by protecting them from oxidation.

Surprisingly, it has now been found that sugar alcohols also ensure a good storage life, but have a lower hygroscopicity than sugar in a carrier matrix in the present application. Thus, an improved moisture and oxygen stable food composition can be obtained using a carbohydrate matrix. In addition, it was surprisingly found that sugar alcohols can better release both the flavouring substances in the carbohydrate matrix and the flavours of the core component of the food composition according to the invention. In particular, this composition with sugar alcohol in the carbohydrate matrix leads to an improved coincident, i.e. simultaneous taste perception of the aroma and the taste of the core component. As a result, hygroscopic core materials such as citric acid can be effectively encapsulated, and a moisture barrier can be built up which nevertheless leads to a coincident and congruent release of the core material and the encapsulation. Thus, a particularly intensive and authentic sensory perception can be achieved.

The sugar alcohol used in the invention is selected from the group consisting of mannitol, isomalt, lactitol, sorbitol, xylitol, threitol, erythritol and arabitol. The preferred sugar alcohol for the carbohydrate matrix is mannitol. Mannitol is particularly preferred for the production of the carbohydrate matrix.

Sugar alcohol is contained in the carbohydrate matrix in an amount of 0.1 to 20% by weight, based on the total weight of the carbohydrate matrix. Preferably, the sugar alcohol content is in the range of 1 to 10 wt. % and most preferably in the range of 5 to 6 wt. %. Amounts of more than 30% by weight of sugar alcohol in the carbohydrate matrix lead to re-crystallization and thus to agglomeration of the food composition.

The carbohydrate matrix also includes at least one carrier into which the other components of the coating are mixed.

The carrier is selected from the group consisting of polysaccharides, gums, plant slime, proteins and mixtures thereof. Preferably the carrier is selected from the group consisting of chemically, physically or enzymatically modified starches, dextran, alginates such as propylene glycol alginate, agar agar, modified celluloses such as methyl cellulose, ethyl cellulose, hydroxyethyl cellulose, hydroxypropyl cellulose, hydroxypropyl methyl cellulose, carboxymethyl cellulose, *psyllium*, fucellan, xanthan gum, nutriose, gum arabic, acacia gum, ghatti, karaya, tragacanth, carrageenan, guar gum, locust bean gum, inulin, curdian, pectins such as low methoxy pectin, gelatine and mixtures thereof.

Gum arabic or gum arabic mixed with other excipients is the most preferred carrier material. Due to its structure, oily flavouring substances or aromas can be emulsified particularly well in gum arabic.

The carriers listed above serve as carriers for the flavouring substances or aromas. They are characterised by a high binding capacity of flavouring substances, a good retention capacity for flavouring substances, excellent solubility, low viscosity with a high solids content, as emulsion stabilisers in the production of the food composition according to the invention and their wide use in foodstuffs. Some of the above-mentioned carriers, for example gum arabic, are also thickeners or gel formers. These properties make the present components particularly suitable for the production of the food composition according to the invention.

The task of the carriers is to provide the best possible protection of the flavouring substances or aromas in the carbohydrate matrix in order to ensure maximum shelf life of the food composition. This is achieved on the one hand by the high binding of flavouring substances in the matrix, which minimises flavour losses during the production process. At the same time, a high loading of the carbohydrate matrix with flavouring substances or aromas is made possible. On the other hand, a high retention capacity of the carriers maximises the retention of volatile flavours during storage, thus ensuring a high recovery of the flavourings. As emulsion stabilizers, they ensure an even distribution of the aroma substances or aromas in the carbohydrate matrix.

The proportion of carrier material is 5 to 40% by weight, preferably 10 to 20%) by weight, based on the total weight of the carbohydrate matrix. A ratio of carrier substance to aroma of 1:1, plus/minus 10% deviation in both directions has proven to be particularly advantageous.

The selection and content of the carriers and the associated properties can control or influence the release of the flavouring and aromatic substances from the food composition according to the invention, for example by reducing or increasing the proportion of gel-forming or thickening carriers such as gum arabic. A reduction of gel-forming carriers such as gum arabic leads to a faster dissolution of the carbohydrate matrix. An increase in the content of gel-forming carriers leads to a slower release of flavouring and aromatic substances, which results in a so-called "longlasting" effect. Such a "longlasting" effect is desired in chewing gum or chewy sweets, where the taste impression is to last for a longer period of time.

In addition to the above-mentioned carriers, the carbohydrate matrix also contains a film-forming component. Maltodextrins and dextrins have proven to be the particularly preferred film-forming components in the production of the food composition according to the invention, as they increase the integration of the flavouring substances or aromas in the carbohydrate matrix and ensure their uniform dispersion in the carbohydrate matrix. In sugar-free foods, resistant dextrin can be used as a filler instead of maltodextrins.

Maltodextrin, dextrin or glucose syrup is a water-soluble carbohydrate mixture produced by hydrolysis of starch and is a mixture of monomers, dimers, oligomers and polymers of glucose. Depending on the degree of hydrolysis, the percentage composition varies. This is described by the dextrose equivalent. According to the invention, maltodextrins, dextrins or glucose syrups are used which are produced from wheat, corn, potatoes, rice, peas, soya, lupines or tapioca and whose dextrose equivalent is between 2 and 30, preferably between 8 and 20 and most preferably between 18 and 20.

The use of maltodextrin or (resistant) dextrin has the effect of reducing the proportion of other carriers in the carbohydrate matrix. For example, the proportion of gel-forming gum arabic in the carbohydrate matrix can be reduced, resulting in a faster dissolution of the shell matrix. This is desirable because rapid dissolution of the shell matrix accelerates flavour release and at the same time the flavour of the core component can be perceived. In general, a low proportion of gel-forming carriers is therefore desirable.

The proportion of the film-forming component such as maltodextrin or dextrin is 20 to 95% by weight, even more preferably 35 to 65% by weight and most preferably <51% by weight, based on the total weight of the carbohydrate matrix.

Optionally, the food composition according to the invention, preferably the coating of the food composition according to the invention, comprises further ingredients selected from the group consisting of: food colorants, preservatives, antioxidants, acidity regulators, sweeteners, emulsifiers, stabilizers, thickeners, gelling agents, anti-caking agents, anti-caking agents, flavor enhancers, sweeteners, vitamins, buffers, plant extracts, flavor with modifying properties, approved additives and food supplements. Such ingredients are known from the state of the art.

FIGS. 1 and 2 are schematic representations of the food composition according to the invention. In the food composition shown in FIG. 1, the core consists of a single flavour particle, whereas in FIG. 2 the core consists of an agglomeration of flavour particles.

When chewing or consuming the food composition according to the invention, both the core component and the flavouring substance are released coincidentally from the carbohydrate matrix in an aqueous environment, whereby the maximum taste effect on releasing the core component and the maximum taste effect on releasing the flavour from the carbohydrate matrix is achieved coincidentally and congruently. With the simultaneous and congruent release of the flavor from the core component and the aroma from the carbohydrate matrix, a coincident and congruent sensory development can be realized, which reproduces the natural taste of a fruit very well and which also lasts during decay. This avoids that the aroma taste develops first and only then afterwards the acidic taste develops during consumption, i.e. that aroma substances or aromas and flavourings are perceived with a time delay.

The same effect occurs, for example, with instant beverages produced with the food compositions according to the invention with the addition of water. A simultaneous release of flavouring and aromatic substances also leads here to a congruent occurrence of the flavour effect of the core component (e.g. citric acid) with the flavour effect from the carbohydrate matrix (e.g. strawberry flavour).

The food composition according to the invention is thus characterized by the fact that the maximum flavor effect by release of the core component and the maximum flavor effect by release of the aromatic taste from the carbohydrate matrix are coincident and congruent when exposed to an aqueous environment and possibly consumed with chewing.

A coincident and congruent taste effect is understood to mean that the curve of the sensory development for the core component and the curve of the sensory development for the aroma component of the food composition according to the invention deviate from each other on average over all measuring times by a maximum of 10% on the respective taste intensity scale, preferably by a maximum of 5%. In particular, the intensity measurement should at no time deviate by more than 20%, preferably 15%.

Figure 3:
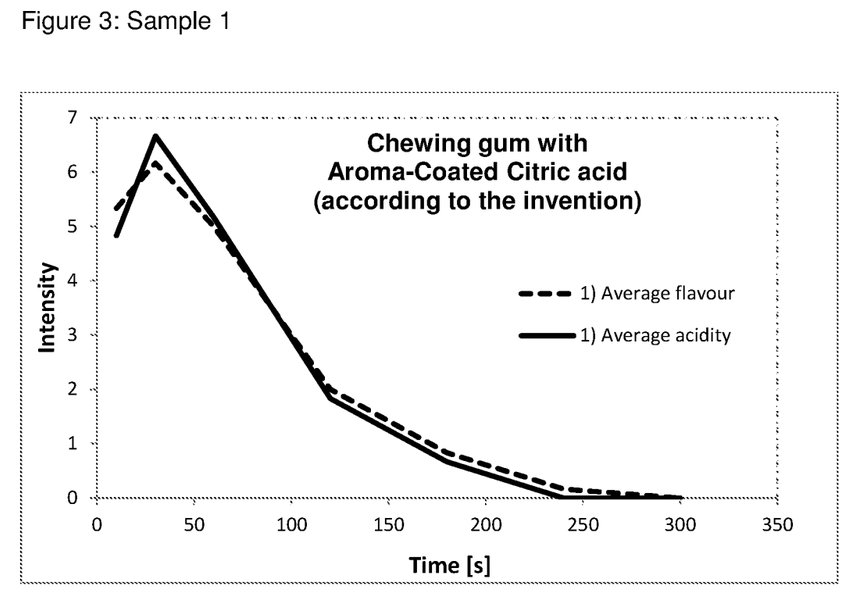
FIG. 3 is a diagram of the sensory development of a food composition according to the invention.
Figure 4:
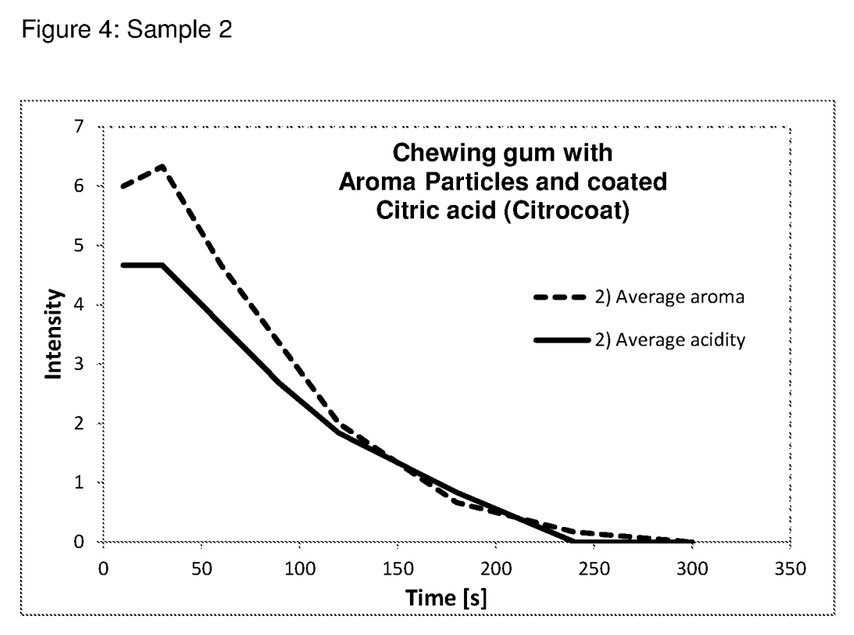
FIG. 4 is a diagram of the sensory response of a food composition not in accordance with the invention.
Figure 5:
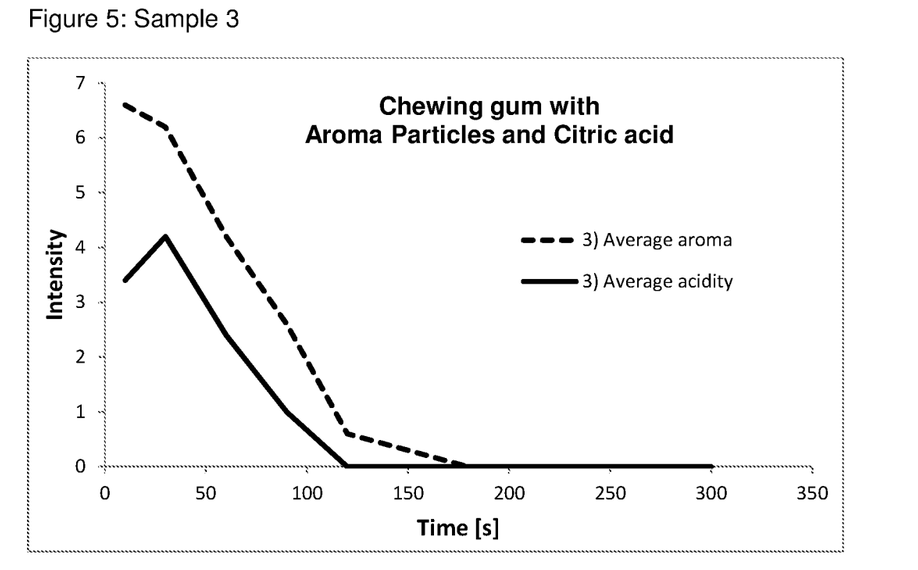
FIG. 5 is a diagram of the sensory response of a food composition not in accordance with the invention

The effect described above is illustrated by the following tables 1 to 3 (samples 1 to 3) in conjunction with FIGS. 3 to 5 as examples.

Tables 1 to 3 (samples 1 to 3) show the aroma evaluation as well as the acidity evaluation of chewing gum samples over time. The aroma dosage data are listed for each sample.

Sample 1 concerns a chewing gum manufactured using the food composition identified as 'Sour Strawberry Flavouring', in accordance with the terms of the invention. With regard to the chewing gum composition, reference is made to the recipe in Table 4 below. The preparation of the food composition designated "Sour Strawberry Flavouring" is as follows: Preparation of an aroma emulsion from

| | 1250 g | WATER |
|---|---|---|
| in which | | |
| | 75 g | MANNITOL |
| | 225 g | RUBBER ARABICUM |
| | 500 g | MALTODEXTRIN |
| are dissolved at room temperature and then | | |
| | 200 g | STRAWBERRY AROMA |
| is emulsified therein. | | |

As the core component, 1000 g of citric acid crystals are coated with the aforementioned aroma emulsion. For this purpose, the citric acid crystals are fluidized in the fluidized bed and then sprayed with the aroma emulsion through one or more nozzles. Due to the temperature prevailing in the fluidized bed below the melting or glass transition temperature of the essential emulsion components, the aqueous aroma emulsion is dried so that a coating layer is formed around the citric acid crystals.

Sample 2 concerns a chewing gum comprising strawberry flavour particles as the flavouring component and additionally (separately) wax-coated citric acid (citric acid with 20% carnauba wax by weight). With regard to the chewing gum composition, reference is made to the formulation in Table 5 below. Citrocoat is a citric acid coated with 20% carnauba wax by weight.

An aroma emulsion is prepared from

| | 1250 g | WATER |
|---|---|---|
| in which | | |
| | 75 g | MANNITOL |
| | 225 g | RUBBER ARABICUM |
| | 500 g | MALTODEXTRIN |
| is dissolved at room temperature and then | | |
| | 100 g | STRAWBERRY AROMA |
| is emulsified therein. | | |

The aroma emulsion is processed by spray granulation with internal nucleation to particles with an average grain size of 0.9 mm.

Production of chewing gum see Table 4-6:
Block A is tempered to 50° C. in a kneader,
then
Block B is premixed and kneaded in the kneader
After the mass becomes homogeneous
Block C is premixed and homogeneously kneaded in the kneader
Then
Block D is added and homogeneously distributed.
The chewing gum is then formed into strips.

Sample 3 concerns a chewing gum containing strawberry flavour particles and citric acid as flavouring ingredient. For the chewing gum composition, reference is made to the formulation in Table 6 below.

To establish the sensory profile, the chewing gum samples were prepared simultaneously with samples 1 to 3 above. The samples were coded, tasted in a sensory room on the same day in a randomised sequence, excluding disturbing influences such as colour, noise and foreign odours. The final result is determined by summing the individual results and then forming the arithmetic mean and is presented graphically in the form of a diagram. The tasting was carried out by an expert panel (6 persons); the intensity scale was set from 0 to 10 (10=very intense; 0=not perceptible)

The average aroma rating and the average acidity rating over time are plotted in FIGS. 3 to 5 as intensities on a scale of 1 to 7.

TABLE 1

| Time [s] | Average aroma | Average acidity |
|---|---|---|
| Sample 1) Sour Strawberry flavour, dosage 1.0% by weight in chewing gum | | |
| Impact | 10 | 5.3 | 4.8 |
| 30 sec | 30 | 6.2 | 6.7 |
| 1 min | 60 | 5.0 | 5.2 |
| 1.5 min | 90 | 3.5 | 3.5 |
| 2 min | 120 | 2.0 | 1.8 |
| 3 min | 180 | 0.8 | 0.7 |
| 4 min | 240 | 0.2 | 0.0 |
| 5 min | 300 | 0.0 | 0.0 |

TABLE 1-continued

| | Time [s] | Average aroma | Average acidity |
|---|---|---|---|
| Sample 2) Strawberry flavour particles, dosage 1.0% by weight and wax-coated citric acid, dosage 0.59% by weight in chewing gum, see above | | | |
| Impact | 10 | 6.0 | 4.7 |
| 30 sec | 30 | 6.3 | 4.7 |
| 1 min | 60 | 4.7 | 3.7 |
| 1.5 min | 90 | 3.3 | 2.7 |
| 2 min | 120 | 2.0 | 1.8 |
| 3 min | 180 | 0.7 | 0.8 |
| 4 min | 240 | 0.2 | 0.0 |
| 5 min | 300 | 0.0 | 0.0 |
| Sample 3) Strawberry flavour particles, dosage 1.0% by weight and citric acid particles 0.475% by weight in chewing gum | | | |
| Impact | 10 | 6.6 | 3.4 |
| 30 sec | 30 | 6.2 | 4.2 |
| 1 min | 60 | 4.2 | 2.4 |
| 1.5 min | 90 | 2.6 | 1 |
| 2 min | 120 | 0.6 | 0 |
| 3 min | 180 | 0 | 0 |
| 4 min | 240 | 0 | 0 |
| 5 min | 300 | 0 | 0 |

As can be seen from FIGS. 3 to 5, the sensory comparison of chewing gum samples 1 to 3 shows that the chewing gum with the food composition according to the invention (sample 1: Sour Strawberry flavour: aroma-coated citric acid) the time course of the sensory perception of the taste (acid) and the aroma (strawberry aroma) are congruent, whereas in the sensory evaluation of the chewing gums containing the acid and the aroma as separate substances (sample 2: Strawberry aroma particles plus wax-coated citric acid; and sample 3: Strawberry aroma particles plus citric acid), the time course of the sensory perception of the taste and aroma diverge. A comparison between sample 2 with wax-coated citric acid and sample 1 with aroma-coated citric acid shows that it is also advantageous that the aroma is present in the coating.

Furthermore, it can be seen that with the food composition used according to the invention, the long-lasting taste effect can generally be improved (comparison of samples 1, 2 with sample 3). However, the taste development of sample 2 (and especially sample 3) does not coincide in the initial period. This can only be achieved with the aroma-encapsulated citric acid after the invention (sample 1).

It can thus be concluded that with the food composition according to the invention, a synergistic taste effect is produced by the simultaneous release of the core component and the aroma from the carbohydrate matrix and a "longlasting effect", i.e. a longer perception of the taste impression, is achieved.

Another subject of the present invention is a process for the production of the food composition according to the invention, comprising the steps
(i) providing an emulsion comprising a carbohydrate matrix in which at least one flavoring agent is included, and the carbohydrate matrix comprises at least one sugar alcohol present in an amount of 0.1 to 20% by weight based on the total weight of the carbohydrate matrix;
(ii) applying the emulsion provided in step (i) to the core component by spray coating; and
(iii) drying of the food composition obtained in step (ii)
(iv) if necessary, repeat steps (ii) and (iii) continuously.

In the process for the preparation of the food composition according to the invention, an emulsion is prepared with water from the components for the carbohydrate matrix, the sugar alcohol and the flavouring or aromatic substances. The emulsion thus produced is applied by means of a spray coating process, preferably in a fluidized bed, to the core components in a coating manner. The core components are moved in the fluidized bed and sprayed with the emulsion. The aqueous solvent of the emulsion evaporates and the solid contained in the emulsion forms the coating.

Depending on the direction from which the particle is sprayed, the coating can be applied using the top spray, tangential spray, bottom spray, the so-called "spouted bed" process or the rotor process.

The process according to the invention can be carried out discontinuously or continuously. Preferably, the process according to the invention is carried out continuously.

The loading of core components in the food composition according to the present invention is 99% by weight, preferably 40 to 60% by weight and most preferably at least 50% by weight, based on the total weight of the food composition, in the process according to the invention. On the other hand, with a spray coating according to the state of the art, only a loading of 5 to 7% by weight is possible, since, for example, with a higher fruit acid content, a spray coating is no longer possible due to sticking.

Spray coating in the fluidized bed is carried out at a temperature in the range of 2 to 200° C. For this purpose, hot air with a gas inlet temperature of 200° C. is fed into the system. In general, the temperature for spray coating in the fluidized bed in the process according to the invention is oriented to the melting point or glass transition temperature of the essential emulsion components. Preferably, spray coating in the fluidized bed is carried out at a temperature 5° C. below the melting point or glass transition temperature of the emulsion components, i.e. in the case of citric acid in a temperature range of 40 to 90° C. and further preferably in the range of 65 to 75° C.

The drying of the food composition claimed in the invention takes place during the manufacturing process, because otherwise the particles would stick together. The drying of the food composition is carried out at a product temperature in the range of 20° C. to 150° C., preferably in a temperature range of 45 to 55° C.

The food composition is produced with an "Aeromatic Strea1" at 80° C. supply air temperature and a drying air volume of 80 m³/h. The spray emulsion was added at a rate of 26 g/min.

As the residence time in the fluidized bed system can be controlled, the coating with the emulsion can be continued until the required particle size has been reached. In accordance with the invention, the loading of the core component with the carbohydrate matrix after spray coating is up to 80 wt. %, based on the total weight of the food composition obtained by the spray coating process.

Due to the selection of the process parameters for spray coating and the composition of the coating, the core components, e.g. citric acid crystals, do not stick together, which would otherwise lead to agglomeration.

The present invention also concerns a food composition obtainable by the method described above.

The food composition is characterised by the following properties:
   high concentration of the flavour component in the core component can be realised, i.e. very high loading in the core component<99%, preferably 30 to 70%, even more preferably 60%, instead of approx. 5% in comparable food compositions produced by spray coating
   Flavour in the core and aroma substances dissolve simultaneously; thus, a congruent sensory process can be realised, which leads to a very realistic sensory perception of fruit (fruit aroma with fruit acid) and which also lasts during the decay of the taste impression;

Leads to an improvement in the "long-lasting" effect, for example in chewing gum, which leads to a longer perception of the taste impression;

the core components can be individually coated (wrapped).

The food composition claimed in the invention may be used in the manufacture of a food or drink. In particular, the food composition according to the invention is used for flavouring or reconstituting the flavour of food, beverage products, semi-finished products, oral hygiene products, cosmetic or pharmaceutical products or of products for animal nutrition.

The use of the food composition according to the invention has proved to be particularly advantageous for effervescent powder as well as instant drinks, instant coffee, confectionery, sweets such as chewy sweets, chewing gum, bakery products, muesli, cereals, muesli bars, tea, fruit tea, dried soups, cornflakes, popcorn, noodles and rice. An example is the chewing gum composition according to Table 4.

In particular, the food composition according to the invention allows for fields of application in which a fat-coated citric acid cannot be used, for example in the production of chewing gum.

Another subject matter of the present invention are foods comprising the food composition according to the invention. The foodstuff contains the food composition according to the invention preferably in a range of 0.05 to 30% by weight, depending on the nature of the foodstuff and the degree of the desired taste intensity in the end product.

The foods to which the food composition according to the invention is added are selected from the group consisting of effervescent powders as well as instant beverages, instant coffee, confectionery, sweets such as chewy sweets, chewing gum, bakery products, muesli, cereals, cereal bars, tea, fruit tea, dried soups, cornflakes, popcorn, noodles and rice.

In the following, the following expertly used terms are used:

Neosorb (solution)=Sorbitol (solution)
Xylisorb=Xylitol
coated Aspartame 20% loaded in Wax=Aspartame with 80% Carnaubawax gecoatet
coated Acesulfame K 25% loaded in Wax=Acesulfame K with 75% Carnaubawax gecoatet
Citrocoat is a citric acid coated with 20% carnauba wax by weight.

TABLE 4

Exemplary recipe of a chewing gum

| Block A | | |
|---|---|---|
| Gum Base | (Gum base Co./ Cafosa Gum) | 20.00 |
| Block B | | |
| Neosorb ® P | (Roquette) | 49.36 |
| Isomalt ST-PF | (Beneo) | 3.00 |
| Xylisorb ® | (Roquette) | 5.00 |
| Mannitol D MSF | (ingredient) | 5.00 |
| coated Aspartame 20% loaded in Wax | (taste tec UK) | 0.12 |
| coated Acesulfame K 25% loaded in Wax | (taste tec UK) | 0.10 |
| Aspartame | (Helm AG) | 0.06 |
| Acesulfame K | (OskarBerg GmbH) | 0.06 |
| Emulpur (soy lecithin) | (Cargill) | 0.30 |

TABLE 4-continued

Exemplary recipe of a chewing gum

| Block C | | |
|---|---|---|
| Neosorb ® solution | (Roquette) | 12.00 |
| Glycerine | (August Hedinger GmbH) | 4.00 |
| Block D | | |
| Sour Strawberry Aroma | (Symrise AG) | 1.00 |

TABLE 5

| Block A | | |
|---|---|---|
| Gum Base | (Gum base Co./ Cafosa Gum) | 20.00 |
| Block B | | |
| Neosorb ® P | (Roquette) | 48.77 |
| Isomalt ST-PF | (Beneo) | 3.00 |
| Xylisorb ® | (Roquette) | 5.00 |
| Mannitol D MSF | (Ingredient) | 5.00 |
| coated Aspartame 20% loaded in Wax | (taste tec UK) | 0.12 |
| coated Acesulfame K 25% loaded in Wax | (taste tec UK) | 0.10 |
| Aspartame | (Helm AG) | 0.06 |
| Acesulfame K | (OskarBerg GmbH) | 0.06 |
| Emulpur (soy lecithin) | (Cargill) | 0.30 |
| Block C | | |
| Neosorb ® solution | (Roquette) | 12.00 |
| Glycerine | (August Hedinger GmbH) | 4.00 |
| Block D | | |
| Evogran ® Strawberry | (Symrise AG) | 1.00 |
| Citrocoat | | 0.59 |

TABLE 6

| Block A | | |
|---|---|---|
| Gum Base | (Gum base Co./ Cafosa Gum) | 20.00 |
| Block B | | |
| Neosorb ® P | (Roquette) | 48.8856 |
| Isomalt ST-PF | (Beneo) | 3.00 |
| Xylisorb ® | (Roquette) | 5.00 |
| Mannitol D MSF | (Ingredient) | 5.00 |
| coated Aspartame 20% loaded in Wax | (taste tec UK) | 0.12 |
| coated Acesulfame K 25% loaded in Wax | (taste tec UK) | 0.10 |
| Aspartame | (Helm AG) | 0.06 |
| Acesulfame K | (OskarBerg GmbH) | 0.06 |
| Emulpur (soy lecithin) | (Cargill) | 0.30 |
| Block C | | |
| Neosorb ® solution | (Roquette) | 12.00 |
| Glycerine | (August Hedinger GmbH) | 4.00 |
| Block D | | |
| Evogran ® Strawberry | (Symrise AG) | 1.00 |
| Citric acid | | 0.475 |

LIST OF REFERENCE SIGNS

1 food composition
2 core component
3 coating

The invention claimed is:

1. A food composition comprising:
   a core component comprising at least one substance selected from the group consisting of fruit acids, ascorbic acid, NaCl, and menthol, and
   a coating,
   wherein the coating comprises a carbohydrate matrix in which at least one flavouring agent is enclosed, and the carbohydrate matrix comprises at least one sugar alcohol present in an amount of 0.1 to 20% by weight based on the total weight of the carbohydrate matrix.

2. The food composition according to claim 1, wherein the fruit acid is one or more selected from the group consisting of: malic acid, citric acid, fumaric acid, gluconic acid, glycolic acid, a-hydroxycaprylic acid, lactic acid, mandelic acid, tartaric acid, oxalic acid, and salicylic acid, enantiomers and salts thereof.

3. A food composition according to claim 1, wherein the core component has an average particle size of 0.1 mm to 10 mm.

4. A food composition according to claim 1, wherein the at least one flavouring agent is a flavouring compound and/or at least one flavour.

5. A food composition according to claim 1, wherein the sugar alcohol is selected from one or more in the group consisting of mannitol, isomalt, lactitol, sorbitol, xylitol, threitol, erythritol and arabitol.

6. A food composition according to claim 1, wherein the carbohydrate matrix further comprises a carrier.

7. A food composition according to claim 6, wherein the carrier is selected from the group consisting of: polysaccharides, gums, vegetable mucilages, proteins and mixtures thereof, chemically, physically or enzymatically modified starches, dextran, alginates, agar agar, modified celluloses psyllium, fucellan, xanthan gum, nutriose, gum arabic, acacia gum, ghatti, karaya, tragacanth, carrageenan, guar gum, locust bean gum, inulin, curdian, pectins, gelatine and mixtures thereof.

8. A food composition according to claim 6, wherein the proportion of carrier, is 5 to 80% by weight, based on the total weight of the carbohydrate matrix.

9. A food composition according to claim 1, wherein the carbohydrate matrix further comprises a film-forming component.

10. A food composition according to claim 9, wherein the proportion of film-forming component is 20 to 95 wt. %, based on the total weight of the carbohydrate matrix.

11. A food composition according to claim 9, wherein the film-forming component comprises a maltodextrin, wherein the maltodextrin is selected from one or more in the group consisting of maltodextrin from wheat, corn, potatoes, rice, peas, soy, lupins and tapioca.

12. A food composition according to claim 1, comprising one or more other ingredients selected from the group consisting of food colours, preservatives, antioxidants, acidity regulators, sweeteners, emulsifiers, stabilizers, thickeners, gelling agents, anti-caking agents, flavour enhancers, vitamins, buffers, plant extracts, flavour with modifying properties, additives and food supplements.

13. A food composition according to claim 1, wherein a maximum taste effect by release of the core ingredient and a maximum taste effect by release of the flavouring agent from the carbohydrate matrix are coincident and congruent when exposed to an aqueous environment.

14. A food composition according to claim 1, wherein a flavouring action of the core component and a flavouring action of an aromatic flavour from the carbohydrate matrix have a synergistic taste effect.

15. A process for preparing the food composition according to claim 1, comprising
   (i) providing an emulsion comprising a carbohydrate matrix in which at least one flavouring agent is enclosed, and the carbohydrate matrix comprises at least one sugar alcohol present in an amount of 0.1 to 20% by weight based on the total weight of the carbohydrate matrix;
   (ii) applying the emulsion provided in step (i) to a core component by spray coating;
   (iii) drying the composition obtained in step (ii).

16. A process according to claim 15, characterized in that the spray coating is a spray coating in a fluidized bed.

17. A food composition obtainable by a manufacturing process according to claim 15.

18. A method of using the food composition according to claim 1 to produce a foodstuff, beverage product, semi-finished product, oral hygiene product, cosmetic, pharmaceutical product or product for animal nutrition.

19. A food or beverage comprising a food composition according to claim 1 in an amount of 0.05 to 30% by weight based on the total weight of the food or beverage.

20. A food or beverage according to claim 19, wherein the food is selected from one or more in the group consisting of: effervescent powder, instant beverages, instant coffee, confectionery, sweets, chewy sweets, chewing gum, baked goods, cereals, cereal bars, tea, fruit tea, dry soups, cornflakes, popcorn, noodles and rice.

21. A food composition according to claim 8, wherein the carrier comprises gum arabic and the proportion of gum arabic is 5 to 80% by weight, based on the total weight of the carbohydrate matrix.

22. The food composition according to claim 7, wherein the carrier is selected from one or more in the group of methyl cellulose, ethyl cellulose, hydroxyethyl cellulose, hydroxypropyl cellulose, hydroxypropyl methyl cellulose, and carboxymethyl cellulose.

* * * * *

UNITED STATES PATENT AND TRADEMARK OFFICE
CERTIFICATE OF CORRECTION

PATENT NO. : 11,291,234 B2
APPLICATION NO. : 16/956205
DATED : April 5, 2022
INVENTOR(S) : Jens-Michael Hilmer et al.

It is certified that error appears in the above-identified patent and that said Letters Patent is hereby corrected as shown below:

In the Claims

At Column 15, Line 5, "NaCI," should be -- NaCl, --.

At Column 15, Line 15, "a-hydroxycaprylic" should be -- α-hydroxycaprylic --.

Signed and Sealed this
Sixth Day of December, 2022

Katherine Kelly Vidal
*Director of the United States Patent and Trademark Office*